(12) United States Patent
Rege et al.

(10) Patent No.: US 11,026,871 B2
(45) Date of Patent: *Jun. 8, 2021

(54) ORAL CARE COMPOSITIONS AND METHODS OF USING THE COMPOSITIONS

(71) Applicant: Colgate-Palmolive Company, New York, NY (US)

(72) Inventors: Aarti Rege, East Windsor, NJ (US); Richard Sullivan, Atlantic Highlands, NJ (US); David Suriano, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,531

(22) PCT Filed: Oct. 8, 2015

(86) PCT No.: PCT/US2015/054792
§ 371 (c)(1),
(2) Date: Apr. 6, 2018

(87) PCT Pub. No.: WO2017/062021
PCT Pub. Date: Apr. 13, 2017

(65) Prior Publication Data
US 2018/0280264 A1  Oct. 4, 2018

(51) Int. Cl.
*A61K 8/27* (2006.01)
*A61K 8/25* (2006.01)
*A61Q 11/00* (2006.01)
*A61K 8/19* (2006.01)
*A61K 8/02* (2006.01)
*A61K 8/04* (2006.01)
*A61K 8/21* (2006.01)
*A61K 8/24* (2006.01)

(52) U.S. Cl.
CPC .............. *A61K 8/27* (2013.01); *A61K 8/0204* (2013.01); *A61K 8/042* (2013.01); *A61K 8/19* (2013.01); *A61K 8/21* (2013.01); *A61K 8/24* (2013.01); *A61K 8/25* (2013.01); *A61Q 11/00* (2013.01); *A61K 2800/28* (2013.01); *A61K 2800/74* (2013.01)

(58) Field of Classification Search
CPC ... A61K 8/27; A61K 8/25; A61K 8/24; A61K 8/21; A61K 8/0204; A61K 8/042; A61K 2800/74; A61K 2800/28; A61Q 11/00
See application file for complete search history.

(56) References Cited

U.S. PATENT DOCUMENTS

| 3,746,555 | A | 7/1973 | Muhler |
|---|---|---|---|
| 6,221,340 | B1 | 4/2001 | Yu et al. |
| 8,980,229 | B2 | 3/2015 | Pilch et al. |
| 9,149,419 | B2 | 10/2015 | Butler et al. |
| 9,717,929 | B2 | 8/2017 | Chopra et al. |
| 10,098,822 | B2 | 10/2018 | Rege et al. |
| 10,154,948 | B2 | 12/2018 | Vemishetti et al. |
| 10,172,770 | B2 | 1/2019 | Rege |
| 10,179,098 | B2 | 1/2019 | Rege et al. |
| 10,258,551 | B2 | 4/2019 | Rege et al. |
| 10,278,906 | B2 | 5/2019 | Rege et al. |
| 10,406,087 | B2 | 9/2019 | Rege et al. |
| 2008/0138298 | A1* | 6/2008 | Glandorf .................. A61K 8/27 424/52 |
| 2012/0308491 | A1 | 12/2012 | Shastry |
| 2013/0251772 | A1 | 9/2013 | Chopra et al. |
| 2014/0227202 | A1 | 8/2014 | Pilgaonkar et al. |
| 2015/0305993 | A1 | 10/2015 | Rege |
| 2015/0328094 | A1 | 11/2015 | Xu et al. |
| 2017/0367949 | A1 | 12/2017 | Rege et al. |
| 2018/0168957 | A1 | 6/2018 | Rege et al. |
| 2019/0029935 | A1 | 1/2019 | Rege et al. |
| 2019/0110965 | A1 | 4/2019 | Rege |
| 2019/0133903 | A1 | 5/2019 | Vemishetti et al. |
| 2019/0192394 | A1 | 6/2019 | Rege et al. |
| 2019/0192395 | A1 | 6/2019 | Rege et al. |

FOREIGN PATENT DOCUMENTS

| CA | 2634758 | 7/2007 |
|---|---|---|
| GB | 1373001 | 11/1974 |
| JP | 2007-327000 | 12/2007 |
| WO | 2014/056713 | 4/2014 |
| WO | WO 2014/088573 | * 6/2014 |

OTHER PUBLICATIONS

Anonymous, "Colgate Enamel Health Whitening Toothpaste, Clean Mint Paste 5.5 oz (155g)," www.Drugstore.com, http://www.drugstore.com/colgate-enamel-health-whitening-toothpaste-clean-mint-paste/qxp532832?catid=183827, accessed Apr. 9, 2015, pp. 1-3.

Colgate-Palmolive, 2014, "Clean Mint Whitening Anticavity Fluoride Toothpaste," Database GNPD Mintel AN 2715919.

Huber Engineered Materials, "Guidelines for Choosing a Huber Cleaning Silica," http://www.hubermaterials.com/products/silica-and-silicates/dental-silicas/formulation-considerations/guidelines-for-choosing-a-huber-dental-cleaning-silica.aspx, accessed Mar. 25, 2015, pp. 1-2.

International Search Report and Written Opinion of the International Searching Authority in International Application No. PCT/US2015/054792, dated Feb. 23, 2016.

(Continued)

*Primary Examiner* — Lezah Roberts

(57) ABSTRACT

An oral care composition is disclosed. The composition comprises zinc phosphate and a silicate compound comprising a metallic element that in cationic form is capable of reducing tooth enamel erosion. The zinc phosphate is added to the oral care composition as a preformed salt. Methods of administering the oral care compositions to subjects in need thereof are also disclosed.

15 Claims, No Drawings

(56) References Cited

OTHER PUBLICATIONS

JP2007327000, Yamada Fumitaka, "Inorganic Coating Composition," Dec. 20, 2007, English language machine translation of abstract, Espacenet, date obtained: Apr. 30, 2020, 1 page <https://worldwide.espacenet.com/patent/search/family/038927685/publication/JP2007327000A?q=jp2007327000>.

* cited by examiner

ORAL CARE COMPOSITIONS AND METHODS OF USING THE COMPOSITIONS

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions. Depending upon the relative pH of surrounding saliva, the tooth enamel will lose or gain positively charged ions such as calcium ions. Generally saliva has a pH between 7.2 and 7.4. When the pH is lowered the fluid medium surrounding the tooth becomes undersaturated with respect to tooth mineral phase and the tooth dissolves, releasing calcium and phosphate ions. This damages the enamel and creates a porous, sponge-like roughened surface. If saliva remains acidic over an extended period, then remineralization may not occur, and the tooth will continue to lose minerals, causing the tooth to weaken and ultimately to lose structure.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antimicrobial properties in plaque and caries studies. Calcium sources, such as calcium silicates, have also been used for improving enamel erosion.

Soluble zinc salts, such as zinc citrate, have been used in dentifrice compositions, but have several disadvantages. Zinc ions in solution impart an unpleasant, astringent mouthfeel, so formulations that provide effective levels of zinc, and also have acceptable organoleptic properties, have been difficult to achieve. Moreover, free zinc ions may react with fluoride ions to produce zinc fluoride, which is insoluble and so reduces the availability of both the zinc and the fluoride. Finally, the zinc ions will react with anionic surfactants such as sodium lauryl sulfate, thus interfering with foaming and cleaning.

Zinc phosphate ($Zn_3(PO_4)_2$) is insoluble in water, although soluble in acidic or basic solutions, e.g., solutions of mineral acids, acetic acid, ammonia, or alkali hydroxides. See, e.g., Merck Index, $13^{th}$ Ed. (2001) p. 1812, monograph number 10205. Partly because it is viewed in the art as a generally inert material, it is commonly used in dental cements, for example in cementation of inlays, crowns, bridges, and orthodontic appliances, which are intended to endure in the mouth for many years. Zinc phosphate dental cements are generally prepared by mixing zinc oxide and magnesium oxide powders with a liquid consisting principally of phosphoric acid, water and buffers, so the cement comprising zinc phosphate is formed in situ by reaction with phosphoric acid.

While compounds and compositions for reducing dentinal erosion are available, further reductions in dentinal erosion are desired. Thus, there is a desire for improved oral care compositions for treating and/or reducing tooth enamel erosion.

BRIEF SUMMARY

An embodiment of the present disclosure is directed to an oral care composition. The composition comprises zinc phosphate and a silicate compound comprising a metallic element that in cationic form is capable of reducing tooth enamel erosion. The zinc phosphate is added to the oral care composition as a preformed salt.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An embodiment of the present disclosure is directed to an oral care composition for intermittent use, e.g., daily use, m the form of a dentifrice, gel, lozenge, mint or chewing gum or other suitable oral care formulation. The oral care composition comprises: zinc phosphate, wherein the zinc phosphate is added to the oral care composition as a preformed salt; and a silicate compound comprising a metallic element that in cationic form is capable of reducing tooth enamel erosion. As used herein, the term "preformed salt"—when used in reference to zinc phosphate—means that the zinc phosphate is not formed in situ in the oral care composition, e.g. through the reaction of phosphoric acid and a zinc salt.

Any amount of zinc phosphate that is effective for protecting against enamel erosion and/or providing any of the other benefits described herein can be employed. Examples of suitable amounts of zinc phosphate can range from 0.05 to 5% by weight, such as from 0.1 to 4% by weight or from 0.5 to 3% by weight, or from 0.8 to 2% by weight, relative to the weight of the oral care composition.

The zinc phosphate, when placed in formulation, e.g., at acidic or basic pH, can dissolve sufficiently upon use to provide an effective concentration of zinc ions to the enamel, thereby protecting against erosion, reducing bacterial colonization and biofilm development, and providing enhanced shine to the teeth. In some embodiments, the formulation comprises an amino acid, such as a basic amino acid, e.g., arginine or lysine, which can confer a basic pH to the formulation. It has also been discovered that zinc phosphate in a formulation with a second phosphate source enhances phosphate deposition. As explained in co-pending Application publication WO2014/088573, the disclosure of which is hereby incorporated by reference in its entirety, this is all unexpected in view of the poor solubility of zinc phosphate, and the art-recognized view that it is substantially inert in conditions in the oral cavity, as evidenced by its widespread use in dental cement. At the same time, the formulations containing zinc phosphate do not exhibit the poor taste and mouthfeel, poor fluoride delivery, and poor foaming and cleaning associated with conventional zinc-based oral care products, which use more soluble zinc salts.

The compositions of the present disclosure also include a silicate compound comprising a metallic element (sometimes referred to herein as a metal-containing silicate) that in cationic form is capable of reducing tooth enamel erosion. Examples of suitable metallic elements include calcium, magnesium, zinc, aluminum and combinations thereof. Examples of suitable compounds include calcium silicate and other calcium glass-complexes, such as calcium sodium phosphosilicates; zinc silicate, magnesium silicate, aluminum silicate, magnesium aluminum silicate and mixtures thereof. In an embodiment, the silicate compound is calcium silicate. The calcium silicate can be added to the compositions of the present disclosure in any suitable form, such as a calcium modified silica gel or a precipitated calcium silicate in a dispersion or dry powder form, or any other desired form useful for oral care compositions. Metal-containing silicates, such as calcium silicate, in combination with zinc phosphate have been found by the inventors of the present disclosure to provide enhanced tooth enamel anti-erosion properties.

Any amount of the metal-containing silicates that are effective for enhancing anti-erosion properties and/or providing any of the other benefits described herein can be employed. Examples of suitable amounts of silicates can range from 0.1% to 10% by weight, such as from 1% to 10% by weight, or from 1% to 5% by weight, such as from 2% to 3% by weight, relative to the weight of the oral care composition.

The compositions may optionally comprise additional ingredients suitable for use in oral care compositions. Examples of such ingredients include active agents, such as a fluoride source and/or a phosphate source in addition to zinc phosphate. The compositions may be formulated in a dentifrice base, e.g., comprising abrasives, e.g., silica abrasives, surfactants, foaming agents, vitamins, polymers, enzymes, humectants, thickeners, additional antimicrobial agents, preservatives, flavorings, colorings, and/or combinations thereof. Examples of suitable dentifrice bases are known in the art. Alternatively, the compositions may be formulated as a gel (e.g., for use in a tray), chewing gum, lozenge or mint. Examples of suitable additional ingredients that can be employed in the compositions of the present disclosure are discussed in more detail below.

Active Agents: The compositions of the disclosure may comprise various other agents which are active to protect and enhance the strength and integrity of the enamel and tooth structure and/or to reduce bacteria and associated tooth decay and/or gum disease or to provide other desired benefits. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., from 0.1 to 20 wt % (expressed as weight of free base), e.g., from 1 to 10 wt % for a consumer toothpaste or from 7 to 20 wt % a professional or prescription treatment product.

One example of an antimicrobial active is triclosan, which can be used in any desired concentration. For example, a triclosan toothpaste may contain from 0.1 to 1 wt. %, such as about 0.3 wt. % triclosan, although the concentration may be limited by government regulations. Any other suitable antimicrobial actives can be employed.

Actives for reducing and/or preventing dentinal hypersensitivity can also be employed. One example of such an active is potassium nitrate, which can be used in any therapeutically effective amount. Other suitable actives for treating dentinal hypersensitivity can also be employed.

Fluoride Ion Source: Where fluoride is used as an active, the oral care compositions include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al, the disclosure of each of which is hereby incorporated by reference in their entirety. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the disclosure may also contain a source of fluoride ions or fluorine-providing ingredient in amounts sufficient to supply from 25 ppm to 25000 ppm of fluoride ions, generally at least 500 ppm e.g., from 500 to 2000 ppm, e.g., from 1000 to 1600 ppm, e.g., about 1450 ppm. The appropriate level of fluoride will depend on the particular application. A toothpaste for general consumer use would typically have from 1000 to 1500 ppm, with pediatric toothpaste having somewhat less. A dentifrice or coating for professional application could have as much as 5,000 or even 25,000 ppm fluoride. Fluoride ion sources may be added to the compositions of the disclosure at a level of from 0.01 wt. % to 10 wt. % in one embodiment or from 0.03 wt. % to 5 wt. %, and in another embodiment from t 0.1 wt. % to 1 wt. % by weight of the composition in another embodiment. Weights of fluoride salts to provide the appropriate level of fluoride ion will obviously vary based on the weight of the counterion in the salt.

Amino acids: In some embodiments, the compositions of the disclosure comprise an amino acid. In particular embodiments, the amino acid may be a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of 7 or greater. Accordingly, basic amino acids include, but are not hunted to, arginine, lysine, citrulline, ornithine, creatine, histidine diaminobutanoic acid, diaminoproprionic acid, salts thereof or combinations thereof. In a particular embodiment, the basic amino acids are selected from arginine, citrulline, and ornithine. In certain embodiments, the basic amino acid is arginine, for example, l-arginine, or a salt thereof. In other embodiments, the amino acid is quaternized, e.g., the amino group is additionally substituted to form a quaternary, ammonium moiety, which may form an inner salt with the carboxyl group, for example, betaine (N,N,N-trimethylglycine).

In various embodiments, the amino acid is present in an amount of from 0.5 wt. % to 20 wt. % of the total composition weight, from 0.5 wt. % to 10 wt. % of the total composition weight, for example 1.5 wt. %, 3.75 wt. %, 5 wt. %, or 7.5 wt. % of the total composition weight in the case of a dentifrice.

Abrasives: The compositions of the disclosure can include abrasives. Examples of suitable abrasives include silica abrasives, such as standard cleaning silicas, high cleaning silicas or any other suitable abrasive silicas. Additional examples of abrasives that can be used in addition to or in place of the silica abrasives include, for example, a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Silica abrasive polishing materials useful herein, as well as the other abrasives, generally have an average particle size ranging between 0.1 and 30 microns, such as between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, the disclosures of which are incorporated herein by reference in their entireties. Particular silica xerogels are marketed under the trade name Syloid® by the W. R. Grace Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, the disclosure of which is incorporated herein by reference in its entirety. In certain embodiments, abrasive materials useful in the practice of the oral care compositions in accordance with the disclosure include silica gels and precipitated amorphous silica having an oil absorption value of less than 100 cc/100 g silica and in the range of from 45 cc/100 g to 70 cc/100 g silica. Oil absorption values are measured using the ASTA Rub-Out Method D281. In certain embodiments, the silicas are colloidal particles having an average particle size of from 3 microns to 12 microns, and from 5 to 10 microns. Low oil absorption silica abrasives particularly useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from 7 to 10 microns in diameter, and an oil absorption of less than 70 cc/100 g of silica is an example of a low oil absorption silica abrasive useful in the practice of the present disclosure.

Any suitable amount of silica abrasive can be employed. Examples of suitable amounts include from 5 wt. % to 40 wt. % (dry weight) of silica particles, such as from 15 wt. % to 30 wt. % or from 15 wt. % to 25 wt. %, based on the total weight of the composition.

Foaming agents: The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care compositions of the present disclosure. Polyoxyethylene is also commonly known as polyethylene glycol ("PEG") or polyethylene oxide. The polyoxyethylenes suitable for compositions of the present disclosure will have a molecular weight of from 200,000 to 7,000,000. In one embodiment the molecular weight will be from 600,000 to 2,000,000 and in another embodiment from 800,000 to 1,000,000. Polyox® is the trade name for the high molecular weight polyoxyethylene produced by Union Carbide. The foaming agent, (e.g., polyoxyethylene) may be present in an amount of from 0.1% to 50%, in one embodiment from 0.5% to 20% and in another embodiment from 1% to 10%, or from 2% to 5% by weight of the oral care compositions of the present disclosure.

Surfactants: The compositions of the present disclosure may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH^2)_2OSO_3Na$).
iv. higher alkyl aryl sulfonates such as sodium dodecyl benzene sulfonate (sodium lauryl benzene sultonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. In one embodiment, the anionic surfactant is present in a toothpaste at from 0.3% to 4.5% by weight, e.g., about 1.5%. The compositions of the disclosure may optionally contain mixtures of surfactants, e.g., comprising anionic surfactants and other surfactants that may be anionic, cationic, zwitterionic or nonionic. Generally, suitable surfactants are those which are reasonably stable throughout a wide pH range. Surfactants are described more full, for example, in U.S. Pat. No. 3,959,458, to Agricola et al.; U.S. Pat. No. 3,937,807, to Haefele; and U.S. Pat. No. 4,051,234, to Gieske et al, the disclosures of which are incorporated herein by reference in their entireties. In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. In a particular embodiment, the compositions of the disclosure comprise sodium lauryl sulfate.

The surfactant or mixtures of compatible surfactants that are included in addition to the anionic surfactants can be present in the compositions of the present disclosure in from 0.1% to 5.0%, in another embodiment from 0.3% to 3.0% and in another embodiment from 0.5% to 2.0% by weight of the total composition. These ranges do not include the anionic surfactant amounts.

In an embodiment, the compositions of the present disclosure include a zwitterionic surfactant, for example a betaine surfactant, for example cocamidopropylbetaine, e.g. in an amount of from 0.1% to 4.5% by weight, e.g. 0.5-2% cocamidopropylbetaine.

Tartar control agents: In various embodiments of the present disclosure, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates and diphosphonates. The disclosure thus may comprise phosphate salts in addition to the zinc phosphate. In particular embodiments, these salts are alkali phosphate salts, e.g., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of from 3 to 4 wt % of the sodium phosphate dibasic and from 0.2 to 1 wt. % of each of the pyrophosphates. In another embodiment, the compositions comprise a mixture of tetrasodium pyrophosphate (TSPP) and sodium tripolyphosphate (STPP) ($Na_5P_3O_{10}$), e.g., m proportions of TSPP) at from 0.5 to 5 wt. %, such as from 1 to 2 wt. % and STPP at from 7 wt. % to 10 wt. %, based on the weight of the composition. Such phosphates are provided in an amount effective to reduce erosion of the enamel, to aid in cleaning the teeth, and/or to reduce tartar buildup on the teeth, for example in an amount of from 0.2 to 20 wt. %. e.g., from 1 to 15 wt. %, by weight of the composition.

Flavoring Agents: The oral care compositions of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of from 0.1 to 5% by weight, e.g., from 0.5 to 1.5% by weight.

Polymers: The oral care compositions of the disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, microcrystalline cellulose or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of from 0.5% to 5.0% by weight of the total composition are used.

The compositions of the disclosure may include an anionic polymer, for example in an amount of from 0.05 to 5%. Examples of such agents generally known for use in dentifrice are disclosed in U.S. Pat. Nos. 5,188,821 and 5,192,531, the disclosures of which are incorporated herein by reference in their entireties; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of from 30.000 to 1,000,000, such as from 300,000 to 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0:05 to 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which, readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of from 1,000 to 2,000,000, described in U.S. Pat. No. 4,842,847, Jun. 27, 1989 to Zahid, the disclosure of which is incorporated herein by reference in its entirety. Another useful class of polymeric agents includes polyamino acids containing proportions of anionic surface-active amino acids such as aspartic acid, glutamic acid and phosphoserine, e.g. as disclosed in U.S. Pat. No. 4,866,161, issued to Sikes et al., the disclosure of which is incorporated herein by reference in its entirety.

Water: The oral compositions may comprise significant levels of water. Water employed in the preparation of commercial oral compositions can be deionized (sometimes referred to as demineralized water) and free of organic impurities. The amount of water in the compositions includes the free water which is added plus that amount which is introduced with other materials.

Humectants: Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol, as well as other polyols and mixtures of these humectants. In one embodiment of the disclosure, the principal humectant is one of glycerin, sorbitol or a combination thereof. In an embodiment, the humectant may be present at levels of greater than 25 wt. %, such as from 25 wt. % to 55 wt. %, or from 30 wt. % to 50 wt. %, or from 35 wt. % to 45 wt. %, based on the total weight of the composition.

Other optional ingredients: In addition to the above-described components, the embodiments of this disclosure can contain a variety of optional oral care composition ingredients some of which are described below. Optional ingredients include, for example, but are not limited to, adhesives, sudsing agents, flavoring agents, sweetening agents such as sodium saccharin, additional antiplaque agents, abrasives, aesthetics such as $TiO_2$ coated mica or other coloring agents, such as dyes and/or pigments. Examples of these and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference in their entireties.

In an embodiment, the compositions of the present disclosure are essentially free of, or have only trace amounts of, or do not contain any of: a carboxypeptidase; or a polyphosphorylated inositol compound selected from phytic acid, myo-inositol pentakis(dihydrogen phosphate), myo-inositol tetrakis(dihydrogen phosphate, myo-inositol trikis(dihydrogen phosphate), or an alkali metal, alkaline earth metal or ammonium salt thereof (where the polyphosphorylated inositol compounds are as described in CA 2634758, the disclosure of which is incorporated herein by reference in its entirety). By "essentially free" is meant that the compositions have less than 0.01% by weight of these compounds. By "trace amounts" is meant that the compositions have less than 0.001% by weight of these compounds.

The present application further discloses methods of using the compositions described herein to increase zinc levels in the enamel and to treat, reduce or control the incidence of enamel erosion, comprising applying any of the compositions as described herein to the teeth, e.g., by brushing. In various embodiments, the disclosure provides a method to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of the compositions as described above to the oral cavity of a person in need thereof, e.g., by brushing the teeth one or more times per day with any of the compositions of the present disclosure. The disclosure further provides compositions for use in any of these methods.

EXAMPLES

Example 1

Dentifrice Formulation

Test dentifrices comprising about 1 wt. % zinc phosphate in combination with from 1 to 3 wt. % calcium modified silica gel were prepared in accordance with the following formulation (ingredients by weight of composition):

TABLE 1

| Ingredient | Wt. % |
|---|---|
| PEG600 | ~2.0 |
| Sodium CMC- | ~0.8 |
| Xanthan Gum | ~0.3 |
| Sorbitol | ~37.3-40.0 |
| Glycerin | ~4.0 |
| Sodium Saccharin | ~0.3-0.6 |
| Tetrasodium pyrophosphate (fine) | ~0.5-2.0 |
| High Cleaning Silica | ~10.0 |
| Microcrystalline Cellulose/Sodium CMC NF | ~1.0 |
| Sodium fluoride | ~0.243 |
| Demineralllized Water | QS |
| Titanium dioxide coated mica | ~0.35 |
| Abrasive silica | ~10.0 |
| Potassium Nitrate | ~0-5.0 |
| Thickener silica | ~1.0-1.3 |
| Cocamidopropyl Betaine | ~1.25 |
| Sodium lauryl sulfate | ~1.5 |
| Flavoring | ~1.3-1.8 |
| Zinc Phosphate, Hydrate | ~1.0 |
| Calcium Modified Silica Gel | ~0.1-10.0 |
| Dye | ~0-0.001 |

Example 2

An example dentifrice was made by adding about 3% by weight calcium silicate to a commercially available toothpaste. As a first control sample, the commercial toothpaste without calcium silicate was used. Both the Example 2 toothpaste and the first control sample had a zinc phosphate concentration of about 1% by weight. Another commercially available toothpaste, which included 1100 ppm fluoride and about 1 wt % zinc citrate, was used as a second control sample.

An in vitro methodology was used to determine the enamel protection activity of the formulation prototype of Example 2. Enamel substrates (N=6/8 per cell) were prepared by embedding bovine incisors in methacrylate-based resin and polishing with 600 and 1200 grit carbide paper consecutively. Care was taken not to penetrate the dentin layer while polishing the enamel to a mirror finish. Prior to testing, all enamel substrates were pre-etched with 5% citric acid for 30 sec. Half the side of each substrate was masked with acid resistant tape to protect the surface as control surface. The model used to evaluate the products alternated 1-min product treatment periods with 2-min acid exposure periods according to the daily sequence of T-C-C-C-C-T (T=product treatment, C=acid challenge). The acid challenge was performed with a 1% aqueous solution of citric acid (unbuffered) adjusted to pH=3.8 with NaOH. All enamel substrates were kept in a sterile artificial saliva solution at 37° C. while not undergoing treatment or challenge. This regimen was conducted for a total of five days, at the end of which a microhardness analysis was used to quantify the amount of enamel lost due to erosion on each enamel substrate on the protected and exposed surface. The change in percentage hardness was calculated. Without treatment, using deionized water in place of test dentifrice, the change in percentage hardness was very high, ca. 80%, with slight variation from experiment to experiment depending on the particular substrate.

The dentifrice of Example 2 and both control samples were tested using the above procedure. The Example 2 formula containing both zinc phosphate and calcium silicate was effective against demineralization in this in vitro pH-cycling model designed to investigate the protective effect of treatments on early enamel dissolution, with an average reduction in hardness following repeated acid challenges of only about 80.8 $g/mm^{-2}$, which was less than the average 83.32 $g/mm^{-2}$ reduction in hardness seen for the first control sample using zinc phosphate without calcium silicate, where hardness was determined by the Knoop Hardness HK test. The second control sample gave an average reduction in hardness of about 98.5 $g/mm^{-2}$. Thus the zinc phosphate and calcium silicate formulation of Example 2 was found to be superior to both control samples.

Example 3

Stability Data

Separate dentifrice compositions similar to the formulation shown in Table 1 were made with varying calcium silicate concentrations of approximately 3 wt. %, approximately 2 wt. % and approximately 1 wt. %. Three samples of each formulation were provided and held at three different temperatures, room temperature (approximately 25° C.), approximately 40° C. and approximately 49° C., for a period of three months. The initial fluoride concentration for each sample was measured at the beginning of the study and then was periodically measured after each month of the study. The results showed that in the presence of calcium silicate at the various concentrations, the fluoride concentrations remained sufficiently stable for commercial applications.

What is claimed is:

1. An oral care composition, comprising:
   zinc phosphate, wherein the zinc phosphate is added to the oral care composition as a preformed salt, and wherein the zinc phosphate is in an amount of 1% by weight, relative to the weight of the oral care composition; and
   a silicate compound comprising calcium silicate in an amount of 3% by weight, relative to the weight of the oral care composition, wherein the amount of calcium silicate is effective to reduce tooth enamel erosion.

2. The oral care composition of claim 1, wherein the oral care composition comprises an abrasive.

3. The oral care composition of claim 1, comprising one or more humectants, and one or more surfactants.

4. The oral care composition of claim 1, further comprising an effective amount of a fluoride ion source.

5. The oral care composition of claim 1, further comprising a basic amino acid in free or orally acceptable salt form.

6. The oral care composition of claim 1, further comprising an effective amount of one or more alkali phosphate salts.

7. The oral care composition of claim 1, further comprising a whitening agent.

8. The oral care composition of claim 1, wherein the oral care composition is a dentifrice.

9. The oral care composition of claim 1, further comprising from 1 to 8% by weight alkali phosphate salts selected from sodium phosphate dibasic, potassium phosphate dibasic, dicalcium phosphate dihydrate, tetrasodium pyrophosphate, tetrapotassium pyrophosphate, calcium pyrophosphate, sodium tripolyphosphate, and mixtures of any two or more of these;
   from 0.05 to 0.5% by weight fluoride; and
   a silica abrasive dentifrice base.

10. The oral care composition of claim 1, wherein the oral care composition is a gel.

11. The oral care composition of claim 1, wherein the oral care composition is a lozenge or mint.

12. The oral care composition of claim 1, wherein the oral care composition is a chewing gum.

13. The oral care composition of claim 1, further comprising an effective amount of one or more antimicrobial agents.

14. A method of treating or reducing dental enamel erosion comprising administering a composition according to claim 1 to the oral cavity of a subject in need thereof.

15. The oral care composition of claim 4, wherein the fluoride source is selected from the group consisting of stannous fluoride, sodium fluoride, potassium fluoride, sodium monofluorophosphate, sodium fluoro silicate, ammonium fluorosilicate, amine fluoride, ammonium fluoride, and combinations thereof.

* * * * *

UNITED STATES PATENT AND TRADEMARK OFFICE
CERTIFICATE OF CORRECTION

Page 1 of 1

PATENT NO. : 11,026,871 B2
APPLICATION NO. : 15/766531
DATED : June 8, 2021
INVENTOR(S) : Aarti Rege et al.

It is certified that error appears in the above-identified patent and that said Letters Patent is hereby corrected as shown below:

In the Specification

In Column 4, Line 54, delete "hunted" and insert -- limited --, therefor.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*